United States Patent [19]

Faranda et al.

[11] Patent Number: 5,723,622

[45] Date of Patent: Mar. 3, 1998

[54] SYNTHETIC METHOD FOR MAKING PYRIDIN-PROPYL-SULPHOBETAINE WITHOUT ANY RISKS FOR THE HUMAN BEINGS AND THE ENVIRONMENT

[76] Inventors: Giuseppe Faranda, Via G. Rossini 12, Mesano Boscone; Luciano Antonio Vailati, Via OSuny 2; Claudio Valzesi, Via A. Anfussi, 3, both of Milan; Enrico Borroni, Via I Maggio 2h/H, Brugherio (Gi), all of Italy

[21] Appl. No.: 674,889

[22] Filed: Jul. 3, 1996

[30] Foreign Application Priority Data

Jul. 6, 1995 [IT] Italy .................. MI95A1453

[51] Int. Cl.$^6$ .................................................. C07D 211/70
[52] U.S. Cl. ........................................................ 546/339
[58] Field of Search .................................... 546/339

[56] References Cited

U.S. PATENT DOCUMENTS

| | | | |
|---|---|---|---|
| 4,150,232 | 4/1979 | Pluss et al. | 546/339 |
| 4,270,987 | 6/1981 | Wilmund et al. | 204/49 |
| 4,435,330 | 3/1984 | Falk | 260/458 F |

*Primary Examiner*—C. Warren Ivy
*Assistant Examiner*—Lyman H. Smith
*Attorney, Agent, or Firm*—Bucknam and Archer

[57] ABSTRACT

A synthetic method for making pyridin-propyl-sulphobetaine, without any risks for the human beings and the environment is described. It comprises reacting a pyridine substituted alkyldihalogenide and then sulphonating in water with an alkylhalogenide solvent, so as to provide pyridin-propyl-sulphobetaine which can be separated from water leaving therein water the halogenides.

5 Claims, No Drawings

SYNTHETIC METHOD FOR MAKING PYRIDIN-PROPYL-SULPHOBETAINE WITHOUT ANY RISKS FOR THE HUMAN BEINGS AND THE ENVIRONMENT

BACKGROUND OF THE INVENTION

The present invention relates to a synthesis method for making pyridin-propyl-sulphobutaine without any risks for the human beings and the environment.

As is known, pyridin-propyl-sulphobetaine is a product which is conventionally used in the galvanic process field as an additive for the brilliant electrolytic nickel plating bath assemblies and operating as a smoothing agent in combination with other additive materials comprising, for example, sodium saccharin, acetylenic alcohols, including two or more carbon atoms, with a triple bond.

At present, pyridin-propyl-sulphobetaine is made by reacting propan-sulphone and pyridine with the following reaction formula:

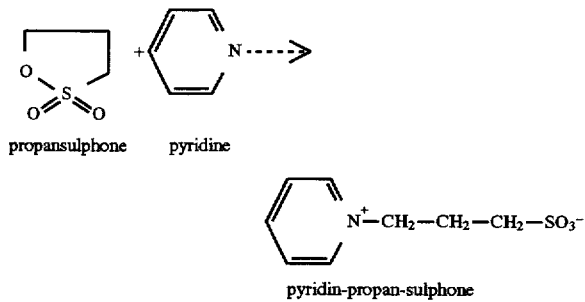

propansulphone   pyridine

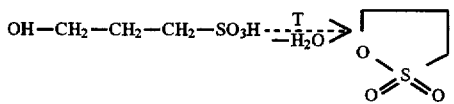

pyridin-propan-sulphone

Propansulphone is made by cyclizing 1-hydroxy-propyl-sulphonic acid, according to the following reaction scheme:

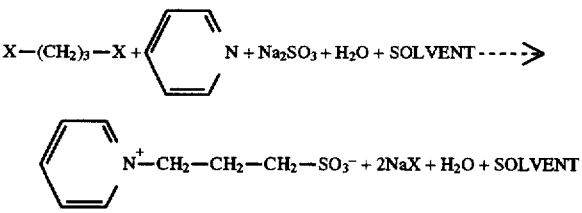

The cyclized ring, called propansulphone is a highly reactive ring, and is a suspected cancerous agent, thereby the making thereof is at present prohibited, with the exception of systems having specifically designed safety characteristics, since, as stated, this substance is very noxious both for the human beings and for the environment.

Accordingly, the systems made for making and using propansulphone have a very high cost and require a lot of monitoring, managing and maintenance operations which negatively affect the cost of the system itself.

SUMMARY OF THE INVENTION

Accordingly, the aim of the present invention is to overcome the above mentioned drawbacks, by providing a novel method for making pyridin-propyl-sulphobetaine which does not use, as an intermediate product, the mentioned propan sulphone.

within the scope of the above mentioned aim, a main object of the present invention is to provide such a method for making pyridin-propyl-sulphobetaine which can be carried out in a very simple and easy manner and which, moreover, provides a product yield from 98% to 100%, the method being therefor very advantageous also from a mere economic standpoint.

Another object of the present invention is to provide such a method for making pyridin-propyl-sulphobetaine which is very safe both for the human beings and for the environment and which, moreover, can be simply carried out.

According to one aspect of the present invention, the above mentioned aim and objects, as well as yet other objects, which will become more apparent hereinafter, are achieved by a method for making pyridin-propyl-sulphobetaine, without any risks for the human beings and environment, characterized in that said method comprises reacting a 1-3 substituted alkyldihalogenide with pyridine and sulphonating, in water, with an alkylhalogenide solvent, to provide pyridin-propyl-sulphobetaine which can be separated from water, leaving in said water the halogenides.

Further characteristics and advantages of the present invention will become more apparent from the following detailed disclosure of the subject synthesis method.

In order to make pyridin-propyl-sulphobetaine without using, as an intermediate product, the mentioned propansulphone, is performed a reaction of a 1-3 substituted alkyldihalogenide with pyridine and the sulphonation according to the thereinbelow reaction scheme:

$$X-(CH_2)_3-X + \langle N \rangle + Na_2SO_3 + H_2O + SOLVENT \longrightarrow$$

$$\langle N^+ \rangle -CH_2-CH_2-CH_2-SO_3^- + 2NaX + H_2O + SOLVENT$$

It should be apparent that this reaction scheme will correspond to a two step reaction, comprising the following two steps:
First step

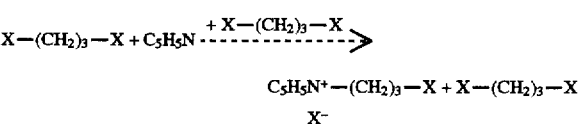

$$C_5H_5N^+ -(CH_2)_3-X + X-(CH_2)_3-X$$
$$X^-$$

Thus the alkyl dihalogenide will operate both as a reagent and a solvent.
Second step

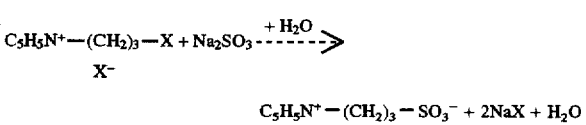

$$C_5H_5N^+ -(CH_2)_3-SO_3^- + 2NaX + H_2O$$

In this formula, X represents iodine, chloride, bromine, whereas the solvent is also constituted by an alkylhalogenide.

The molar ratio of these three components (i.e. 1–3 substituted alkyldihalogenide, pyridine and sodium sulfite), of the reaction is 1:1:1.

The above two reaction steps, which occur with a very high yield ratio, near to 100%, are practically carried out in two stages and, more specifically, in a first stage the first above mentioned step is performed at a temperature from 20° C. and 80° C., with a reaction time from 20 to 100 hours.

The temperature of the second stage, in which the second above mentioned step is performed, is, preferably, though not necessarily, from 50° C. to 90° C.

In the above mentioned formula, the provision of the solvent is very important for increasing the product yield and reaction rate, to provide a reagent material conversion factor of about 100%.

Moreover, all of the intermediate reactions occur with products yields from 98% to 100%, thereby the process is very advantageous also from a mere economic standpoint.

From the above mentioned reaction pyridin-propyl-sulphobetaine is obtained, which is separated from the process water by the fractioned crystallization method and subsequent filtering; the halogenide materials will be left in water; the cationic portion of said halogenides will depend on the sulphide type which is used.

The sulphonation of an alkyl halogenide can be made with a minimum skillness in any chemical laboratory, with a very high yield.

From the above disclosure it should be apparent that the invention fully achieves the intended aim and objects.

In particular, the fact is to be pointed out that a synthesis method has been provided which hallows to make pyridin-propyl-sulphobetaine with a very high yield and purity, and, most importantly, without any risks for the human being and the environment.

The invention as disclosed is susceptible to several modifications and variations, all of which will come within the inventive idea scope.

Moreover, all of the details can be replaced by other technically equivalent elements.

We claim:

1. A synthetic method for making pyridine-propyl-sulphobetaine, without any risks for human beings and environment, wherein said method comprises the steps of reacting a 1-3 substituted alkyldihalogenide with pyridine and sulphonating, in water, with an alkylhalogenide co-solvent, to provide pyridin-propyl-sulphobetaine which can be separated from water, leaving in said water the halogenides.

2. The method according to claim 1 wherein said method comprises the following steps:

first step

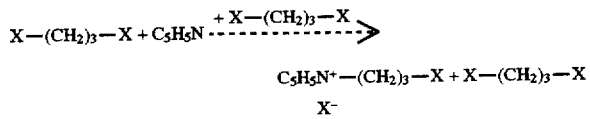

in said first step said 1-3 substituted alkylhalogenide operating both as a reagent and co-solvent, and second step

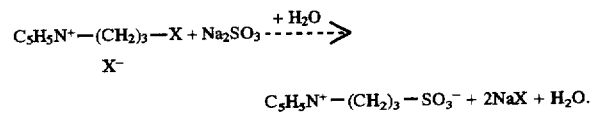

3. The method according to claim 1 wherein said sulphonating step is performed by using sodium sulfite and wherein the molar ratio between the said 1-3 substituted alkyldihalogenide, said pyridine and said sodium sulfite is 1:1:1.

4. The method according claim 2 wherein said two steps are performed in two reaction stages, a first reaction stage, in which is performed said first step, having a temperature from 20° C. to 80° C. and a reaction time from 20 to 100 hours, and a second reaction stage in which is performed said second step having a temperature from 50° C. to 90° C.

5. The method according to claim 1 wherein said pyridin-propyl-sulphobetaine is separated from said water by a fractioned crystallizing and filtering step.

* * * * *